US011961235B2

United States Patent
Jin

(10) Patent No.: US 11,961,235 B2
(45) Date of Patent: Apr. 16, 2024

(54) APPARATUS, METHOD AND RECORDING MEDIUM STORING INSTRUCTIONS FOR DETERMINING BONE AGE OF TEETH

(71) Applicant: BONEWISE INC., Seoul (KR)

(72) Inventor: Dong Kyu Jin, Seoul (KR)

(73) Assignee: BONEWISE INC., Seoul (KR)

( * ) Notice: Subject to any disclaimer, the term of this patent is extended or adjusted under 35 U.S.C. 154(b) by 497 days.

(21) Appl. No.: 17/421,560

(22) PCT Filed: Mar. 25, 2019

(86) PCT No.: PCT/KR2019/003422
§ 371 (c)(1),
(2) Date: Jul. 8, 2021

(87) PCT Pub. No.: WO2020/196939
PCT Pub. Date: Oct. 1, 2020

(65) Prior Publication Data
US 2022/0084205 A1  Mar. 17, 2022

(51) Int. Cl.
G06T 7/00 (2017.01)
A61B 6/51 (2024.01)
(Continued)

(52) U.S. Cl.
CPC .............. G06T 7/0014 (2013.01); A61B 6/51 (2024.01); G06F 18/22 (2023.01); G06T 3/40 (2013.01);
(Continued)

(58) Field of Classification Search
CPC .......... G06T 7/0014; G06T 3/40; G06T 3/60; G06T 7/11; G06T 2207/20081;
(Continued)

(56) References Cited

U.S. PATENT DOCUMENTS 6,350,120 B1 *  2/2002  Sachdeva ................. A61C 7/00
433/24
11,107,218 B2 *  8/2021  Salah .................... G06T 7/0014
(Continued)

FOREIGN PATENT DOCUMENTS

CN      107767376 A    3/2018
JP      2006-527882 A   12/2006
(Continued)

OTHER PUBLICATIONS

Stern, Darko et al, Automatic Age Estimation and Majority Age Classification From Multi-Factorial MRI Data, Jul. 2019, IEEE Journal of Biomedical and Health Informatics vol. 23, No. 4, pp. 1392-1403 (Year: 2019).*

(Continued)

Primary Examiner — Lewis G West
(74) Attorney, Agent, or Firm — Sughrue Mion, PLLC

(57) ABSTRACT

The present disclosure proposes an apparatus for determining a bone age of teeth. The apparatus according to the present disclosure may acquire a plurality of first teeth images of a plurality of teeth corresponding to a first gender and having a first bone age, generate a plurality of pre-processed images by pre-processing the plurality of first teeth images, generate a determination filter for determining a teeth shape for the first bone age of a human body having the first gender by training the neural network model using the plurality of pre-processed images, acquire a second teeth image of teeth of a human body having a second gender and gender information indicating the second gender, and determine a second bone age of the teeth corresponding to the second teeth image based on the second teeth image and the gender information by using the determination filter.

20 Claims, 9 Drawing Sheets

(51) Int. Cl.
  *G06F 18/22* (2023.01)
  *G06T 3/40* (2006.01)
  *G06T 3/60* (2006.01)
  *G06T 7/11* (2017.01)
  *G06V 10/75* (2022.01)

(52) U.S. Cl.
  CPC .................. *G06T 3/60* (2013.01); *G06T 7/11* (2017.01); *G06T 2207/20081* (2013.01); *G06T 2207/20084* (2013.01); *G06T 2207/30036* (2013.01); *G06V 10/759* (2022.01)

(58) Field of Classification Search
  CPC . G06T 2207/20084; G06T 2207/30036; G06T 2207/10116; G06T 7/0012; A61B 6/51; A61B 6/00; A61B 6/501; A61B 6/505; A61B 6/5217; G06F 18/22; G06V 10/759; G06V 10/82; G06V 20/66; G06N 3/04; G06N 3/08; G16H 30/40; G16H 50/20; G16H 50/30; G16H 50/70
  See application file for complete search history.

(56) References Cited

U.S. PATENT DOCUMENTS

| | | |
|---|---|---|
| 2004/0258313 A1 | 12/2004 | Jones et al. |
| 2009/0129639 A1 | 5/2009 | Ortega et al. |
| 2013/0308843 A1 | 11/2013 | Tank |
| 2014/0037180 A1 | 2/2014 | Wang et al. |
| 2014/0227655 A1* | 8/2014 | Andreiko .................. G06T 3/14 433/29 |
| 2016/0124920 A1 | 5/2016 | Golay |
| 2018/0165369 A1 | 6/2018 | Orihara et al. |
| 2018/0232603 A1 | 8/2018 | Shim et al. |
| 2021/0082184 A1* | 3/2021 | Claessen .................. A61B 6/51 |
| 2021/0150702 A1* | 5/2021 | Claessen .................. G06N 3/08 |
| 2021/0174543 A1* | 6/2021 | Claessen .................. G06T 19/20 |
| 2021/0322136 A1* | 10/2021 | Anssari Moin ........ G16H 30/40 |

FOREIGN PATENT DOCUMENTS

| | | |
|---|---|---|
| JP | 2013-541085 A | 11/2013 |
| JP | 2014-509908 A | 4/2014 |
| JP | 2016-67532 A | 5/2016 |
| KR | 10-2017-0016778 A | 2/2017 |
| KR | 10-1779800 B1 | 9/2017 |
| KR | 10-2017-0135572 A | 12/2017 |
| KR | 10-2019-0023003 A | 3/2019 |
| KR | 10-2128997 B1 | 7/2020 |
| WO | 2016/194996 A1 | 12/2016 |
| WO | 2017/222489 A1 | 12/2017 |
| WO | 2018/057714 A1 | 3/2018 |
| WO | 2018/127949 A1 | 7/2018 |

OTHER PUBLICATIONS

Cular, Luka et al, Dental Age Estimation from Panoramic X-Ray images using Statistical Models, Sep. 2017, IEEE 10th Annual Symposium on Image and Signal Processing and Analysis, pp. 25-30 (Year: 2017).*

Communication dated Jul. 19, 2022, issued in Japanese Application No. 2021-541242.

International Search Report for PCT/KR2019/003422 dated Dec. 19, 2019 (PCT/ISA/210).

Čular et al., "Dental age estimation from panoramic X-ray images using statistical models", 10th International Symposium on Image and Signal Processing and Analysis (ISPA 2017), Sep. 18-20, 2017, Ljubljana, Slovenia, pp. 25-30 (7 pages total).

Extended European Search Report dated Nov. 2, 2022 in European Application No. 19921148.3.

Elisabeth Hofmann et al., "Age assessment based on third molar mineralisation", Journal of Orofacial Orthopedics, 2017, vol. 78, No. 2, pp. 97-111 (15 pages total).

* cited by examiner

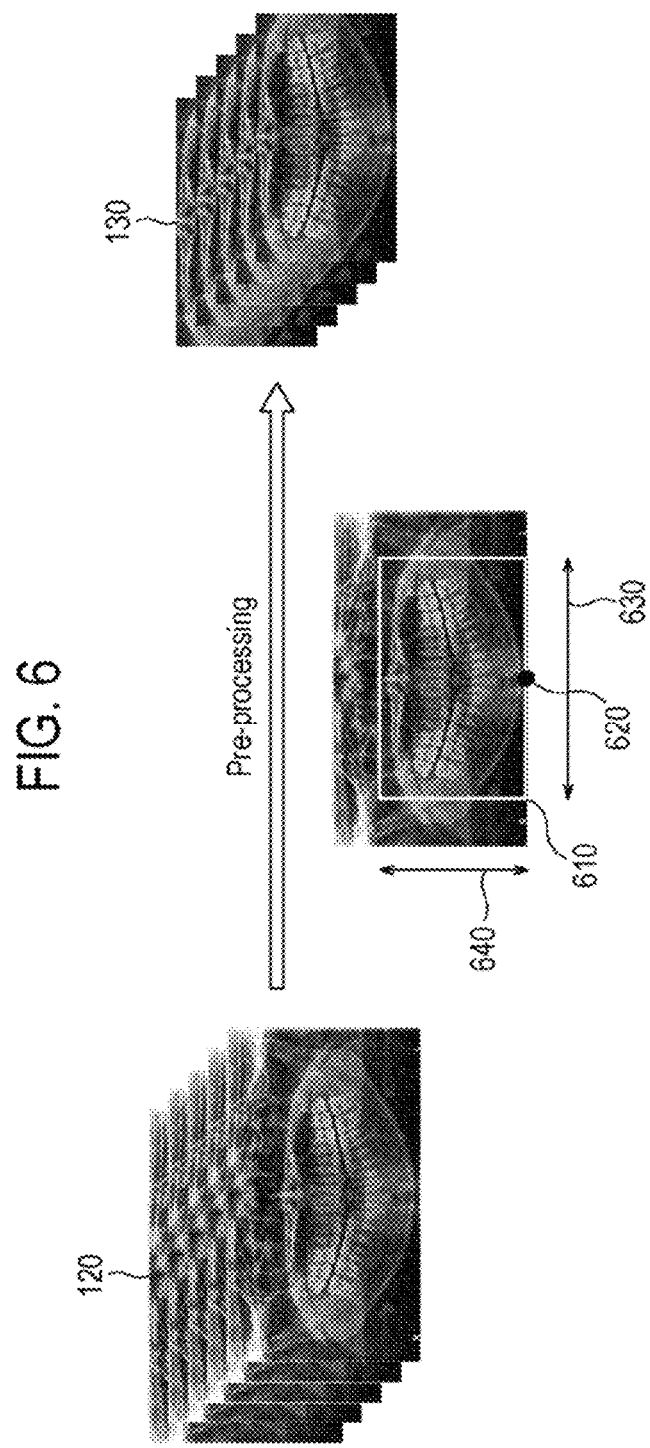

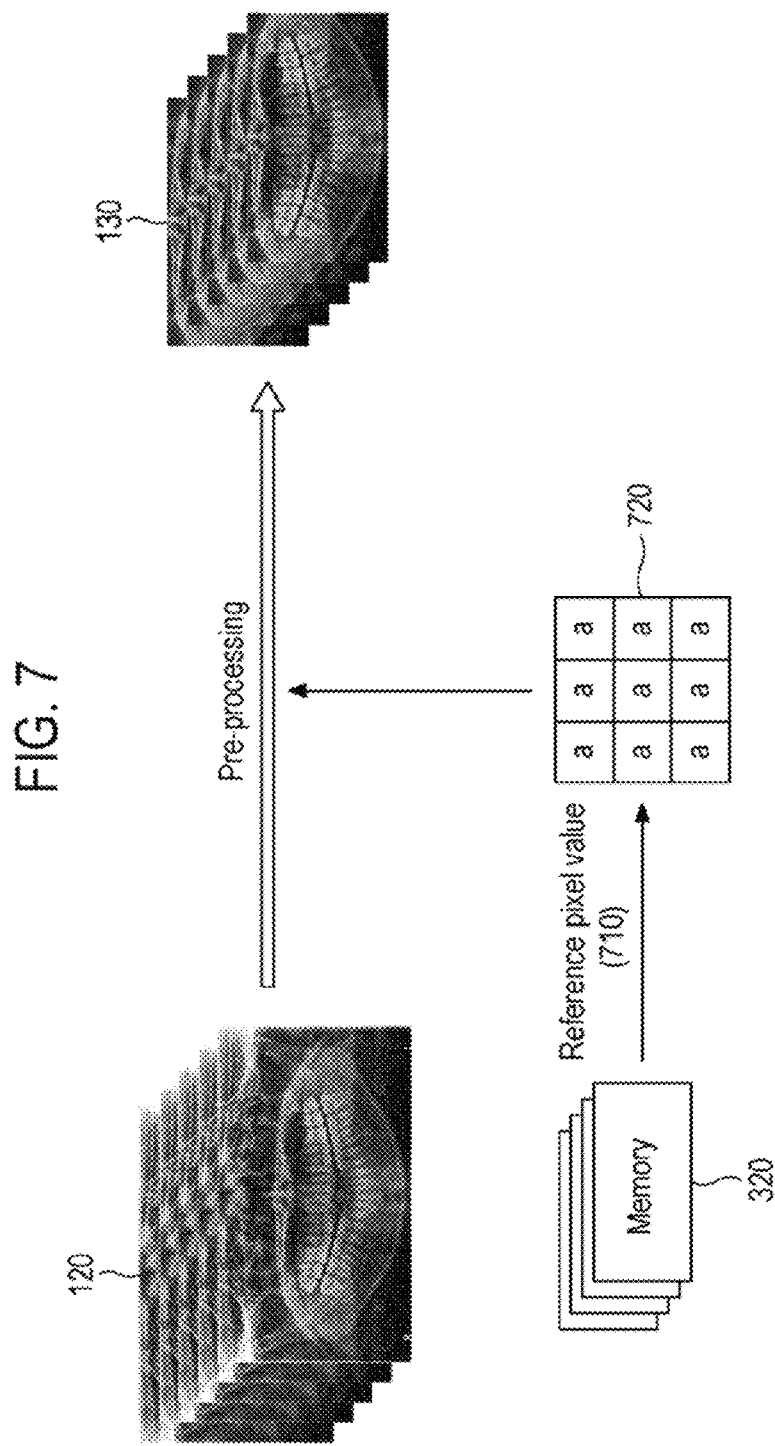

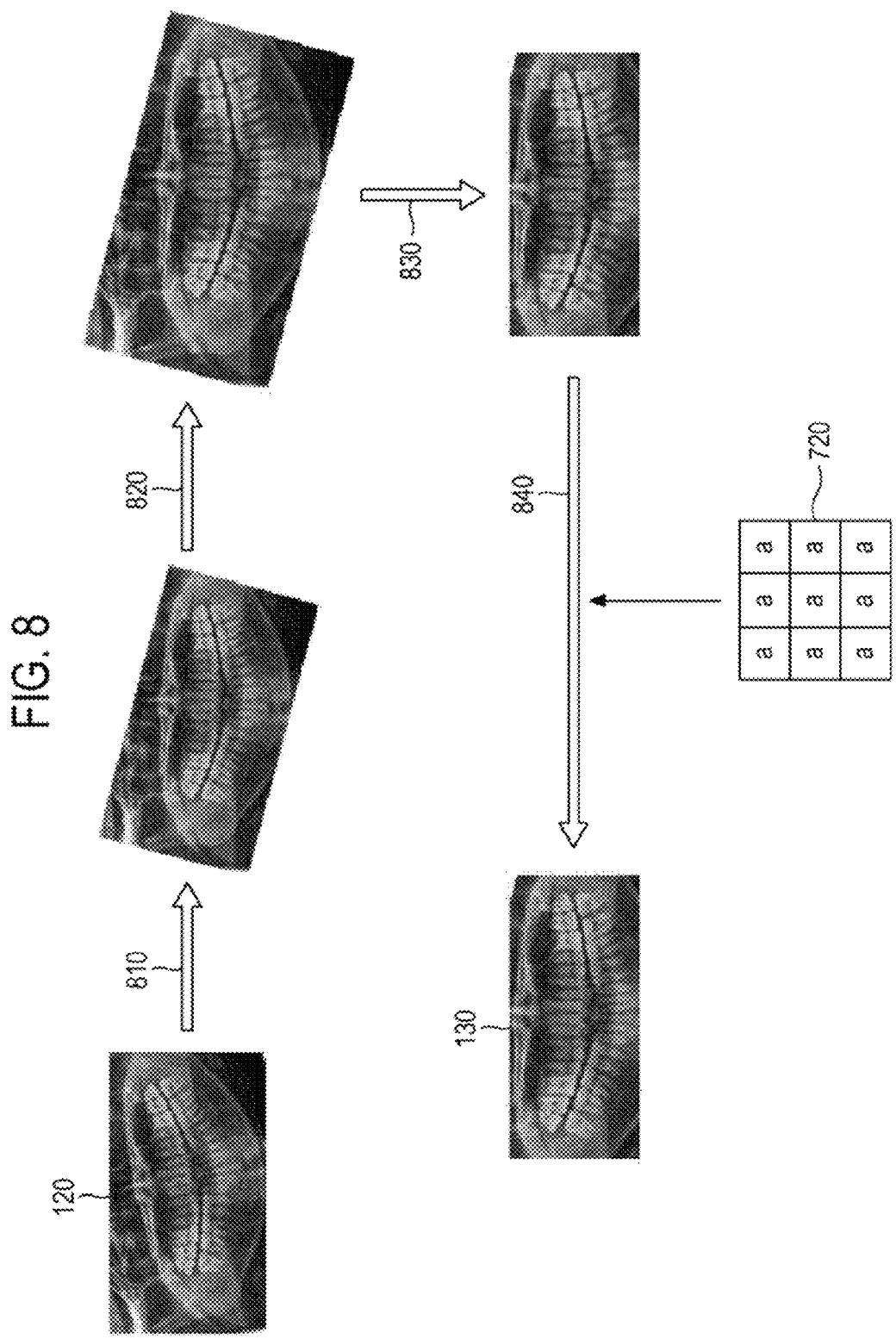

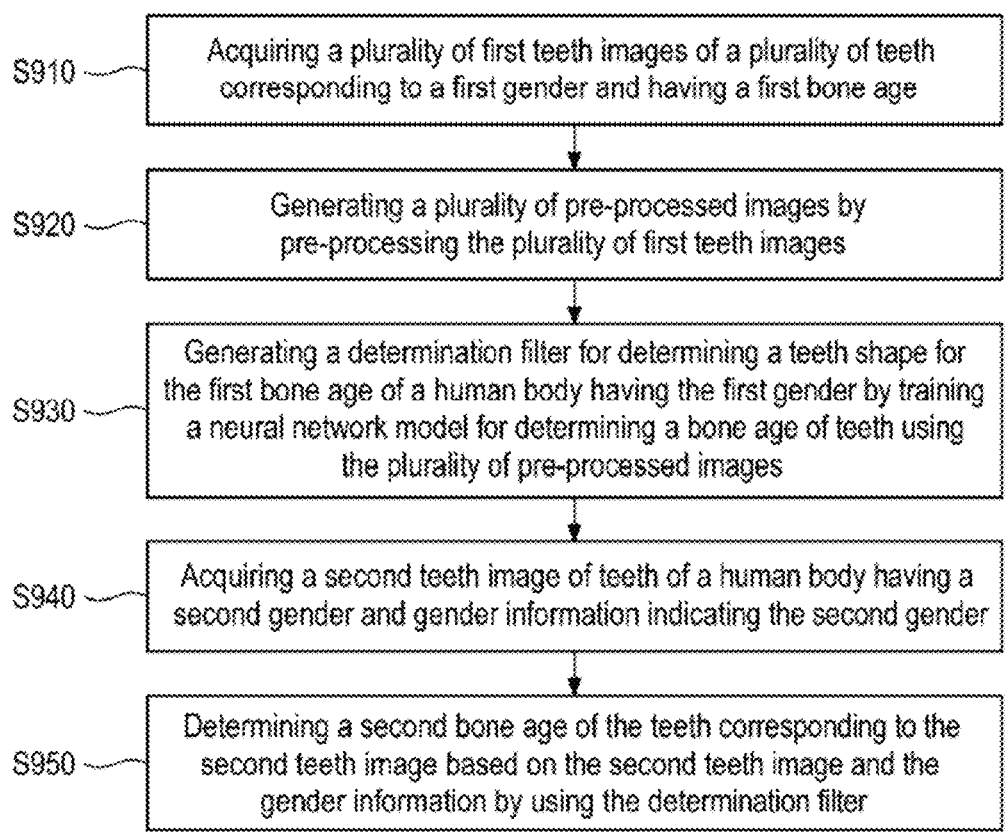

APPARATUS, METHOD AND RECORDING MEDIUM STORING INSTRUCTIONS FOR DETERMINING BONE AGE OF TEETH

CROSS REFERENCE TO RELATED APPLICATIONS

This application is a National Stage of International Application No. PCT/KR2019/003422 filed Mar. 25, 2019, the entire disclosure of which is incorporated herein by reference.

TECHNICAL FIELD

The present disclosure relates to a technique for determining a bone age of teeth.

BACKGROUND

The bone age of teeth may be assessed from an image (e.g., an X-ray image, etc.) of human teeth. By comparing the assessed bone age of the teeth and the actual age of the human body, it can be determined whether the teeth are growing normally as compared to the actual age of the human body. Furthermore, if the teeth are not growing normally, it can be determined how fast or delayed the growth of the teeth is.

In order to determine the bone age of the teeth, an image of the teeth may be analyzed by a human user. The user may compare a teeth image obtained by actually imaging the teeth with a reference image representing each bone age of the teeth, determine a reference image having the most similar bone maturity to the corresponding teeth image from among a plurality of reference images, and determine the teeth bone age corresponding to the determined reference image as a teeth bone age represented by the corresponding teeth image. However, this method has a problem in that the results of bone age analysis on the teeth image may vary depending on the user's ability and expertise. In particular, since the shape of the teeth represented by the teeth image is non-quantified data, the results of the teeth bone age analysis may show a large variation among users. Accordingly, the accuracy and reliability of the analysis result according to the above-described method may be significantly reduced.

SUMMARY

Various embodiments of the present disclosure provide a technique for determining a bone age of teeth.

According to one aspect of the present disclosure, there may be proposed an apparatus for determining a bone age of teeth. The apparatus according to one aspect of the present disclosure may include: one or more processors; and one or more memories configured to store instructions for causing the one or more processors to perform an operation when executed by the one or more processors, and a neural network model for determining a bone age of teeth. The one or more processors may be configured to: acquire a plurality of first teeth images of a plurality of teeth corresponding to a first gender and having a first bone age; generate a plurality of pre-processed images by pre-processing the plurality of first teeth images; generate a determination filter for determining a teeth shape for the first bone age of a human body having the first gender by training the neural network model using the plurality of pre-processed images; acquire a second teeth image of teeth of a human body having a second gender and gender information indicating the second gender; and determine a second bone age of the teeth corresponding to the second teeth image based on the second teeth image and the gender information by using the determination filter.

In one embodiment, the one or more processors may be configured to: determine whether the second gender matches the first gender; upon determining that the second gender matches the first gender, determine whether a region matching the determination filter exists in the second teeth image; and upon determining that the region matching the determination filter exists, determine the first bone age as the second bone age.

In one embodiment, the one or more processors may be configured to: generate a plurality of initial filters including two or more pixels each having a randomly set pixel value; select at least two initial filters each having a matching region in the plurality of pre-processed images from among the plurality of initial filters; repeatedly perform a training operation N times by using the at least two initial filters as first filters, the training operation being an operation that generates combined filters by connecting at least two k-th filters and determines at least two of the combined filters each having a matching region in the plurality of pre-processed images as (k+1)-th filters; and determine one of at least two (N+1)-th filters determined by repeating the training operation as the determination filter, the N being a preset constant.

In one embodiment, the one or more processors may be configured to: in the training operation, generate the combined filters by connecting the at least two k-th filters horizontally or vertically.

In one embodiment, the one or more processors may be configured to: in the training operation, determine whether each of the combined filters has a matching region in the plurality of pre-processed images based on a calculation result between pixel values of a partial region in each of the plurality of pre-processed images and pixel values of each of the combined filters.

In one embodiment, the one or more processors may be configured to: generate the plurality of pre-processed images by removing a region other than a region representing teeth from each of the plurality of first teeth images, and the region representing the teeth may be a region having a preset width and height based on a center point of a lower end of each of the plurality of first teeth images.

In one embodiment, the one or more processors may be configured to: generate the plurality of pre-processed images in a number larger than the number of the plurality of first teeth images by rotating each of the plurality of first teeth images at two or more predetermined angles.

In one embodiment, the one or more processors may be configured to: generate the plurality of pre-processed images in a number larger than the number of the plurality of first teeth images by enlarging or reducing each of the plurality of first teeth images within a range of a preset ratio.

In one embodiment, the one or more memories may be configured to store information indicating a reference pixel value for identifying a preset feature in the plurality of first teeth images, and the one or more processors may be configured to: generate a reference filter including one or more pixels having the reference pixel value; identify a region matching the reference filter in each of the plurality of first teeth images; and generate the plurality of pre-processed images by removing the identified region from each of the plurality of first teeth images.

In one embodiment, the one or more memories may be configured to store information indicating a reference slope and a reference size for teeth shapes of the plurality of pre-processed images, and information indicating a reference pixel value for identifying a preset feature, and the one or more processors may be configured to: rotate each of the plurality of first teeth images so that a teeth shape of each of the plurality of first teeth images has the reference slope; enlarge or reduce each of the plurality of rotated images so that a teeth shape of each of the plurality of rotated images has the reference size; remove a region other than a region representing teeth from each of the plurality of enlarged or reduced images, the region representing the teeth being a region having a preset width and height based on a center point of a lower end of each of the plurality of enlarged or reduced images; and generate the plurality of pre-processed images by removing a region matching the reference filter including one or more pixels having the reference pixel value from each of the plurality of images from which the region other than the region representing the teeth is removed.

According to another aspect of the present disclosure, there may be proposed a method for determining a bone age of teeth. The method according to another aspect of the present disclosure may be a method performed in a computer including one or more processors and one or more memories that are configured to store instructions to be executed by the one or more processors. The method according to one aspect of the present disclosure may include: acquiring a plurality of first teeth images of a plurality of teeth corresponding to a first gender and having a first bone age; generating a plurality of pre-processed images by pre-processing the plurality of first teeth images; generating a determination filter for determining a teeth shape for the first bone age of a human body having the first gender by training a neural network model for determining a bone age of teeth using the plurality of pre-processed images; acquiring a second teeth image of teeth of a human body having a second gender and gender information indicating the second gender; and determining a second bone age of the teeth corresponding to the second teeth image based on the second teeth image and the gender information by using the determination filter.

In one embodiment, determining the second bone age may include: determining whether the second gender matches the first gender; upon determining that the second gender matches the first gender, determining whether a region matching the determination filter exists in the second teeth image; and upon determining that the region matching the determination filter exists, determining the first bone age as the second bone age.

In one embodiment, generating the determination filter may include: generating a plurality of initial filters including two or more pixels each having a randomly set pixel value; selecting at least two initial filters each having a matching region in the plurality of pre-processed images from among the plurality of initial filters; repeatedly performing a training operation N times by using the at least two initial filters as first filters, the training operation being an operation that generates combined filters by connecting at least two k-th filters and determines at least two of the combined filters each having a matching region in the plurality of pre-processed images as (k+1)-th filters; and determining one of at least two (N+1)-th filters determined by repeating the training operation as the determination filter, the N being a preset constant.

In one embodiment, generating the plurality of pre-processed images may include: generating the plurality of pre-processed images by removing a region other than a region representing teeth from each of the plurality of first teeth images, and the region representing the teeth may be a region having a preset width and height based on a center point of a lower end of each of the plurality of first teeth images.

In one embodiment, generating the plurality of pre-processed images may include: generating a reference filter including one or more pixels having a reference pixel value; identifying a region matching the reference filter in each of the plurality of first teeth images; and generating the plurality of pre-processed images by removing the identified region from each of the plurality of first teeth images, and the reference pixel value may be a pixel value for identifying a preset feature in the plurality of first teeth images.

According to another aspect of the present disclosure, there may be proposed a non-transitory computer-readable recording medium that stores instructions for determining a bone age of teeth. The instructions recorded in the recording medium according to another aspect of the present disclosure may be instructions for causing one or more processors to perform an operation when executed by the one or more processors. The instructions may cause the one or more processors to perform: acquiring a plurality of first teeth images of a plurality of teeth corresponding to a first gender and having a first bone age; generating a plurality of pre-processed images by pre-processing the plurality of first teeth images; generating a determination filter for determining a teeth shape for the first bone age of a human body having the first gender by training a neural network model for determining a bone age of teeth using the plurality of pre-processed images; acquiring a second teeth image of teeth of a human body having a second gender and gender information indicating the second gender; and determining a second bone age of the teeth corresponding to the second teeth image based on the second teeth image and the gender information by using the determination filter.

In one embodiment, the instructions may cause the one or more processors to perform: determining whether the second gender matches the first gender; upon determining that the second gender matches the first gender, determining whether a region matching the determination filter exists in the second teeth image; and upon determining that the region matching the determination filter exists, determining the first bone age as the second bone age.

In one embodiment, the instructions may cause the one or more processors to perform: generating a plurality of initial filters including two or more pixels each having a randomly set pixel value; selecting at least two initial filters each having a matching region in the plurality of pre-processed images from among the plurality of initial filters; repeatedly performing a training operation N times by using the at least two initial filters as first filters, the training operation being an operation that generates combined filters by connecting at least two k-th filters and determines at least two of the combined filters each having a matching region in the plurality of pre-processed images as (k+1)-th filters; and determining one of at least two (N+1)-th filters determined by repeating the training operation as the determination filter, the N being a preset constant.

In one embodiment, the instructions may cause the one or more processors to perform: generating the plurality of pre-processed images by removing a region other than a region representing teeth from each of the plurality of first teeth images, and the region representing the teeth may be a region having a preset width and height based on a center point of a lower end of each of the plurality of first teeth images.

In one embodiment, the instructions may cause the one or more processors to perform: generating a reference filter including one or more pixels having a reference pixel value; identifying a region matching the reference filter in each of the plurality of first teeth images; and generating the plurality of pre-processed images by removing the identified region from each of the plurality of first teeth images, and the reference pixel value may be a pixel value for identifying a preset feature in the plurality of first teeth images.

According to various embodiments of the present disclosure, a bone age of corresponding teeth may be determined from a teeth image, which is obtained by imaging teeth, using a neural network model trained according to a deep learning algorithm.

According to various embodiments of the present disclosure, a neural network model may be efficiently trained by pre-processing training data including information such as a teeth image, a gender, a bone age and the like.

According to various embodiments of the present disclosure, the accuracy and reliability of an analysis result for a teeth bone age may be ensured by determining a bone age of teeth using a neural network model.

According to various embodiments of the present disclosure, an analysis result of a patient's teeth bone age may be used for diagnosis of pediatric endocrine diseases (e.g., growth hormone deficiency, precocious puberty, etc.) for the patient.

According to various embodiments of the present disclosure, a bone age of teeth may be assessed based on a panoramic view of teeth captured during orthodontic treatment or dental treatment at a dental clinic, and if there is an abnormality in the bone age, the diagnosis of pediatric endocrine diseases for the patient may be performed in cooperation with the department of pediatric endocrinology.

BRIEF DESCRIPTION OF DRAWINGS

FIG. 6 is a diagram illustrating a process of performing pre-processing by removing a region other than a region representing teeth according to an embodiment of the present disclosure.

FIG. 7 is a diagram illustrating a process of performing pre-processing by removing a portion corresponding to a treatment trace of teeth according to an embodiment of the present disclosure.

FIG. 8 is a diagram illustrating an example of a process of generating a pre-processed image from a first teeth image according to an embodiment of the present disclosure.

FIG. 9 is a diagram illustrating an example of a method for determining a bone age of teeth, which may be performed by the apparatus according to the present disclosure.

DETAILED DESCRIPTION

Figure 1:
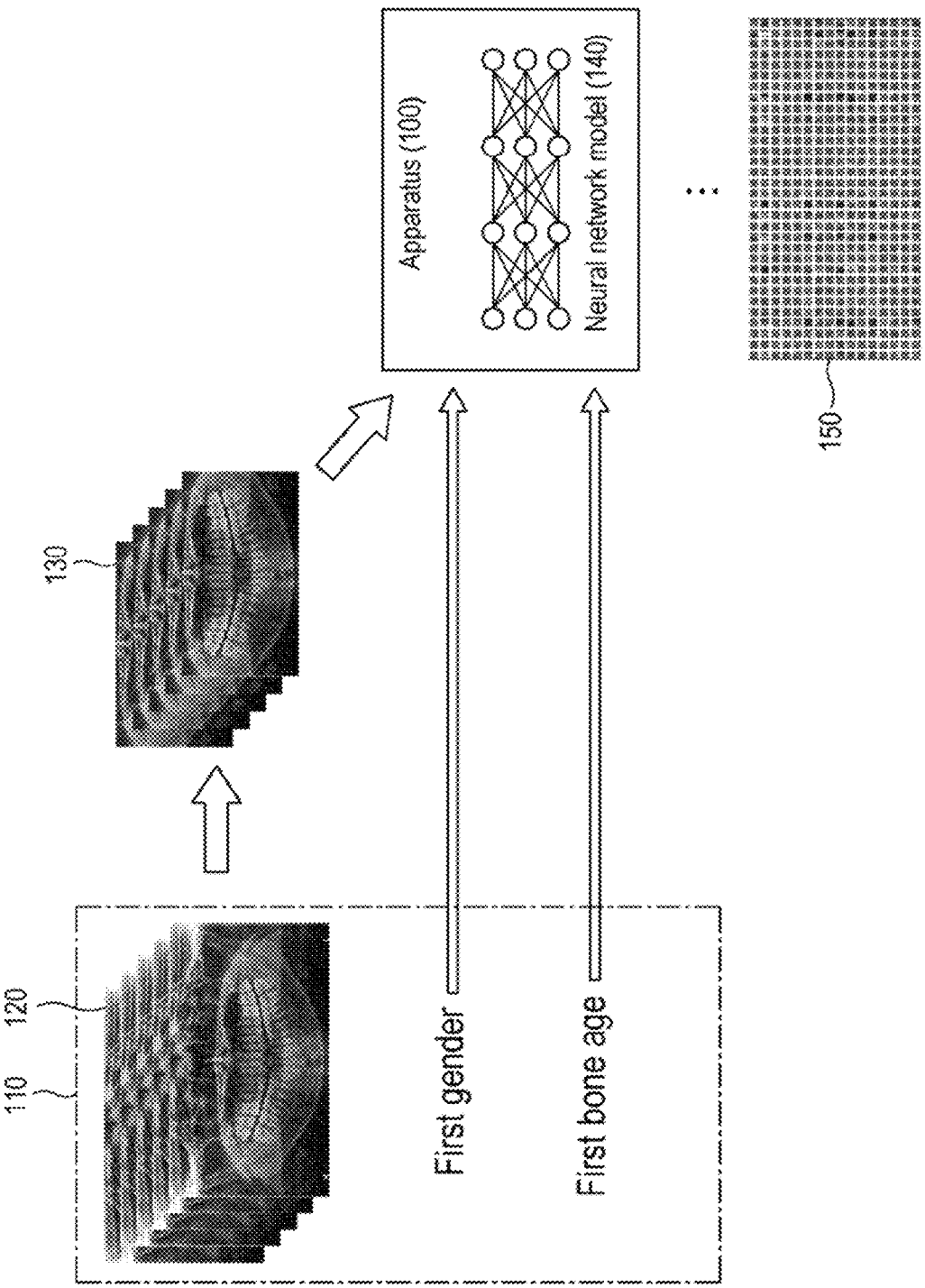
FIG. 1 is a diagram illustrating a process of training a neural network model by an apparatus according to an embodiment of the present disclosure.

The various embodiments described herein are exemplified for the purpose of clearly describing the technical idea of the present disclosure, and are not intended to limit the technical idea of the present disclosure to specific embodiments. The technical idea of the present disclosure includes various modifications, equivalents, alternatives of each of the embodiments described in the present disclosure, and embodiments selectively combined from all or part of the respective embodiments. In addition, the scope of the technical idea of the present disclosure is not limited to various embodiments or detailed descriptions thereof presented below.

The terms used herein, including technical or scientific terms, may have meanings that are generally understood by a person of ordinary skill in the art to which the present disclosure pertains, unless otherwise specified.

As used herein, the expressions such as "include," "may include," "provided with," "may be provided with," "have," and "may have" mean the presence of subject features (e.g., functions, operations, components, etc.) and do not exclude the presence of other additional features. That is, such expressions should be understood as open-ended terms that imply the possibility of including other embodiments.

A singular expression can include meanings of plurality, unless otherwise mentioned, and the same is applied to a singular expression stated in the claims.

The terms "first," "second," etc. used herein are used to distinguish a plurality of components from one another, and are not intended to limit the order or importance of the relevant components.

As used herein, the expressions such as "A, B and C," "A, B or C," "A, B and/or C," "at least one of A, B and C," "at least one of A, B or C," "at least one of A, B and/or C," "at least one selected from A, B and C," "at least one selected from A, B or C," and "at least one selected from A, B and/or C" may mean each of the listed items or all possible combinations of the listed items. For example, the expression "at least one selected from A and B" may refer to (1) A, (2) at least one of A, (3) B, (4) at least one of B, (5) at least one of A and at least one of B, (6) at least one of A and B, (7) at least one of B and A, and (8) A and B.

The expression "based on" or "according to" used herein is used to describe one or more factors that influence a decision, an action of judgment or an operation described in a phrase or sentence including the relevant expression, and this expression does not exclude additional factor influencing the decision, the action of judgment or the operation.

As used herein, the expression that a certain component (e.g., a first component) is "connected" to another component (e.g., a second component) may mean that the certain component is not only connected or coupled to another component directly, but also connected or coupled via another new component (e.g., a third component).

As used herein, the expression "configured to" may have a meaning such as "set to," "having the ability to," "modified to," "made to," "capable of," or the like depending on the context. The expression is not limited to the meaning of "specially designed for hardware." For example, a processor configured to perform a specific operation may mean a generic-purpose processor capable of performing a specific operation by executing software.

Hereinafter, various embodiments of the present disclosure will be described with reference to the accompanying drawings. In the accompanying drawings and the descriptions of the drawings, the same reference numerals may be assigned to the same or substantially equivalent elements. Furthermore, in the following description of various embodiments, redundant descriptions of the same or corresponding elements may be omitted. However, this does not mean that the elements are not included in the embodiments.

FIG. 1 is a diagram illustrating a process of training a neural network model 140 by an apparatus 100 according to an embodiment of the present disclosure. The apparatus 100 according to an embodiment of the present disclosure may train a neural network model for determining a bone age of teeth, and may determine a bone age of target teeth using the neural network model.

Specifically, the apparatus 100 may store a neural network model 140 for determining a bone age of teeth. The apparatus 100 may train the neural network model 140 using training data 110 according to a deep learning algorithm. In the present disclosure, deep learning may mean that computer software improves a data processing ability through learning data and data processing experiences. The neural network model is constructed by modeling the correlation between data, and the correlation of the neural network model may be expressed by a plurality of parameters. The neural network model extracts and analyzes features from given data to derive a correlation between the data. Deep learning or machine learning may mean that the parameters are optimized by repeating this process.

The apparatus 100 may receive training data 110. The training data 110 may include a plurality of teeth images obtained by imaging each of a plurality sets of human teeth. Each of the teeth images may be associated with information on the gender (e.g., male or female) of a human body having the corresponding teeth and information on the actual bone age (e.g., 5.24 years) of the corresponding teeth. In one embodiment, the apparatus 100 may receive, as the training data 110, a plurality of teeth images (hereinafter referred to as first teeth images 120) obtained by imaging teeth corresponding to a human body of one gender (hereinafter referred to as first gender) and having one bone age (hereinafter referred to as first bone age). That is, the apparatus 100 may acquire a plurality of first teeth images 120 obtained by imaging a plurality of teeth corresponding to the first gender and having the first bone age. In the present disclosure, a plurality of teeth images according to different genders and different bone ages may also be inputted to the apparatus 100 and used to train the neural network model 140. However, since these teeth images may be processed by the apparatus 100 similarly to the first teeth images 120 corresponding to the first gender and the first bone age, the technique of the present disclosure will be described below based on the first teeth images 120.

The apparatus 100 may perform pre-processing on each of the first teeth images 120 to generate a plurality of pre-processed images (hereinafter referred to as pre-processed images 130). In the pre-processing process, the apparatus 100 may perform an operation such as rotating each of the first teeth images 120, enlarging/reducing each of the first teeth images 120, or removing unnecessary regions. The specific pre-processing process will be described later. As the pre-processed images 130 pre-processed according to various methods are inputted to the neural network model 140, the learning efficiency of the neural network model 140 for determining the teeth bone age may be enhanced.

The apparatus 100 may train the neural network model 140 using the pre-processed images 130 to generate a determination filter 150 corresponding to the first gender and the first bone age. When the human body having the first gender has teeth corresponding to the first bone age, the determination filter 150 may represent a reference shape of the corresponding teeth. The apparatus 100 may determine whether a teeth image represents the teeth shape for the first gender and the first bone age using the determination filter 150. A detailed process of generating the determination filter 150 will be described later. As described above, by learning teeth images according to various genders and bone ages, it may be possible to generate determination filters according to different genders and bone ages.

Figure 2:
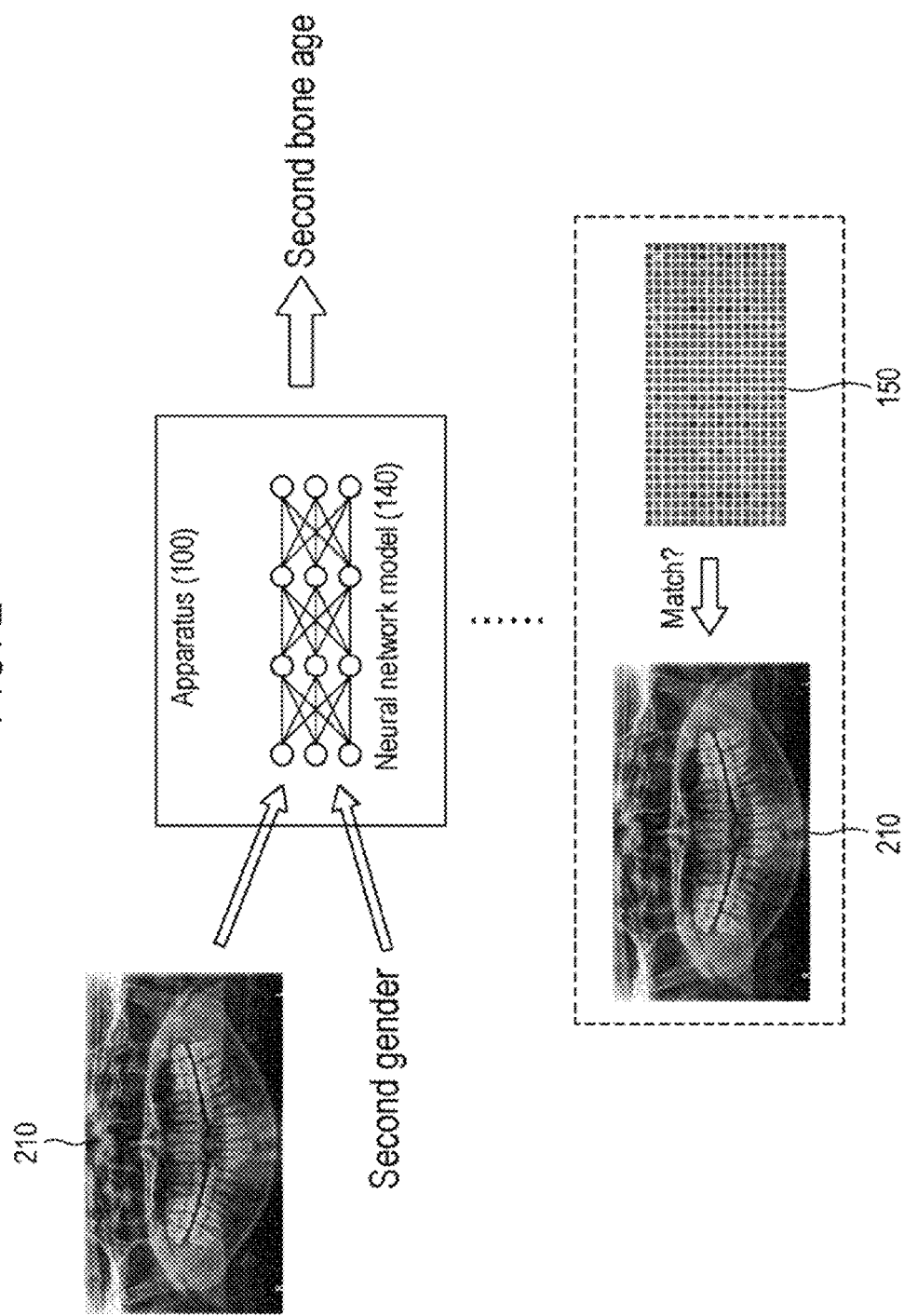
FIG. 2 is a diagram illustrating a process of determining a bone age of corresponding teeth from an inputted teeth image by the apparatus according to an embodiment of the present disclosure.

FIG. 2 is a diagram illustrating a process of determining a bone age of corresponding teeth from an inputted teeth image by the apparatus 100 according to an embodiment of the present disclosure. The apparatus 100 according to the present disclosure may determine a bone age (hereinafter referred to as second bone age) of target teeth represented by a target teeth image (hereinafter referred to as second teeth image 210) inputted to the apparatus 100, using the determination filter 150 generated in the training process of the neural network model 140.

Specifically, the apparatus 100 may receive the second teeth image 210 and the gender information. The second teeth image 210 may be a teeth image obtained by imaging teeth of a human body according to one gender (hereinafter referred to as second gender). The second teeth image 210 may be an image obtained by imaging target teeth for which a teeth bone age is to be assessed. The gender information may be information representing the gender (i.e., the second gender) of the human body corresponding to the second teeth image 210.

The apparatus 100 may determine the second bone age of the teeth corresponding to the second teeth image 210 based on the second teeth image 210 and the gender information by using the determination filter 150. Specifically, the apparatus 100 may determine whether the second gender matches the first gender. If the second gender matches the first gender, the above-described determination filter 150 according to the first gender may be used to determine the bone age. If not, another determination filter may have to be used to determine the bone age. Upon determining that the second gender matches the first gender, the apparatus 100 may compare the second teeth image 210 with the determination filter 150. The apparatus 100 may determine whether a region matching the determination filter 150 exists in the second teeth image 210. The determination of whether to match may be performed by determining whether a region having pixel values that match the pixel values of the region represented by the determination filter 150 exists in the second teeth image 210. In one embodiment, the determination of whether to match may also be performed by determining whether a region having pixel values falling within a preset range based on the pixel values of the determination filter 150 exists in the second teeth image 210.

If a region matching a specific teeth shape represented by the determination filter 150 is found in the second teeth image 210, i.e., if it is determined that a region matching the determination filter 150 exists in the second teeth image 210, the apparatus 100 may determine the first bone age as a second bone age of the second teeth image 210. If there is no region matching the determination filter 150, the apparatus 100 may determine that the second teeth image 210 does not have the first bone age, and may compare the determination filter according to another bone age with the second teeth image 210.

Figure 3:
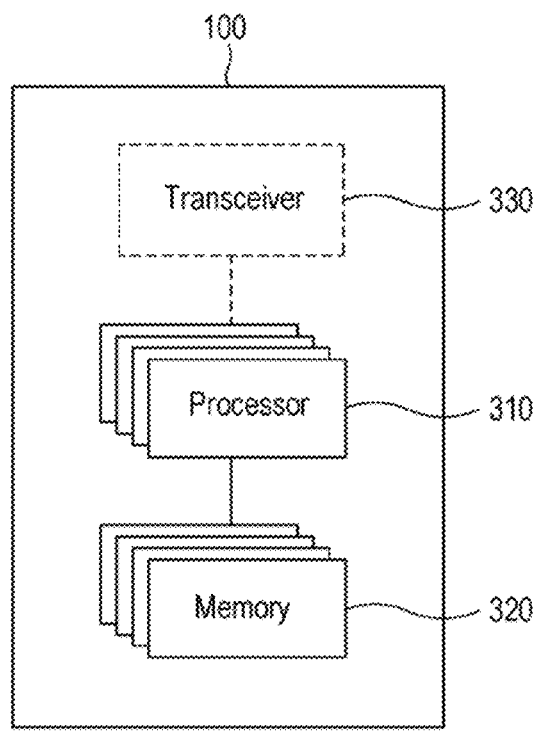
FIG. 3 is a block diagram of the apparatus according to various embodiments of the present disclosure.

FIG. 3 is a block diagram of the apparatus 100 according to various embodiments of the present disclosure. In one embodiment, the apparatus 100 may include one or more processors 310 and/or one or more memories. In one embodiment, at least one of these components of the apparatus 100 may be omitted, or another component may be added to the apparatus 100. In one embodiment, additionally or alternatively, some components may be integrally implemented, or may be implemented as a singular entity or plural entities. In the present disclosure, one or more processors 310 may be referred to as processor 310. The expression "processor 310" may mean a set of one or more processors, unless clearly expressed otherwise in context. In the present disclosure, one or more memories 320 may be referred to as memory 320. The expression "memory 320" may mean a set of one or more memories, unless clearly expressed otherwise in context. In one embodiment, at least some of the internal and external components of the apparatus 100 may be connected to each other through a bus, a general purpose input/output (GPIO), a serial peripheral interface (SPI), a mobile industry processor interface (MIPI), or the like to exchange data and/or signals.

The processor 310 may drive software (e.g., a program) to control at least one component of the apparatus 100 connected to the processor 310. In addition, the processor 310 may perform various operations related to the present disclosure, such as calculation, treatment, data generation, processing, and the like. In addition, the processor 310 may load data or the like from the memory 320, or may store data in the memory 320. The processor 310 may generate each of the pre-processed images 130 by obtaining a plurality of first teeth images 120 and performing pre-processing on each of the first teeth images 120. The processor 310 may generate the above-described determination filter 150 by training the neural network model 140 using the pre-processed images 130. The processor 310 may acquire second teeth images 210 and gender information corresponding to the second teeth images 210, and may determine a second bone age of target teeth corresponding to the second teeth images 210 by using the determination filter 150.

The memory 320 may store various types of data. The data stored in the memory 320 may be the data acquired, processed or used by at least one component of the apparatus 100, and may include software (e.g., instructions, programs, etc.). The memory 320 may include a volatile memory and/or a nonvolatile memory. In the present disclosure, the instructions or the programs may be software stored in the memory 320, and may include an operating system for controlling resources of the apparatus 100, an application, and/or middleware for providing various functions to the application so that the application may utilize the resources of the apparatus. The memory 320 may store the neural network model 140 for determining the bone age of the teeth. In addition, the memory 320 may store instructions for causing the processor 310 to perform an operation (calculation) when executed by the processor 310. In one embodiment, the memory 320 may store a plurality of first teeth images 120, a plurality of pre-processed images 130, one or more deep learning algorithms, a second teeth image 210 and/or gender information corresponding to the second teeth image 210.

In one embodiment, the apparatus 100 may further include a transceiver 330. The transceiver 330 may perform wireless or wired communication between the apparatus 100 and a server, or between the apparatus 100 and another apparatus. For example, the transceiver 330 may perform wireless communication according to a method such as eMBB (enhanced Mobile Broadband), URLLC (Ultra Reliable Low-Latency Communications), MMTC (Massive Machine Type Communications), LTE (long-term evolution), LTE-A (LTE Advance), UMTS (Universal Mobile Telecommunications System), GSM (Global System for Mobile communications), CDMA (code division multiple access), WCDMA (wideband CDMA), WiBro (Wireless Broadband), WiFi (wireless fidelity), Bluetooth, NFC (near field communication), GPS (Global Positioning System), GNSS (global navigation satellite system) or the like. For example, the transceiver 330 may perform wired communication according to a method such as USB (Universal Serial Bus), HDMI (High Definition Multimedia Interface), RS-232 (Recommended Standard-232), POTS (Plain Old Telephone Service) or the like.

In one embodiment, the processor 310 may obtain information from the server by controlling the transceiver 330. The information obtained from the server may be stored in the memory 320. In one embodiment, the information obtained from the server may include a neural network model 140 for determining a bone age of teeth, a plurality of first teeth images 120, one or more deep learning algorithms, a second teeth image 210, and/or gender information corresponding to the second teeth image 210.

In one embodiment, the apparatus 100 may further include an input device (not shown). The input device may be a device that receives data (e.g., the training data 110, the second teeth image 210 and/or the gender information corresponding to the second teeth image 210) to be transmitted from the outside to at least one component of the apparatus 100. For example, the input device may include a mouse, a keyboard, a touch pad and the like. In one embodiment, the apparatus 100 may further include an output device (not shown). The output device may be a device that provides various type of data (e.g., the second bone age, etc.) according to an operation of the apparatus 100 to a user in a visual form. For example, the output device may include a display, a projector and the like.

In one embodiment, the apparatus 100 may be an apparatus of various types. For example, the apparatus 100 may be a portable communication apparatus, a computer apparatus, a portable multimedia apparatus, a wearable apparatus, or an apparatus obtained by combining the aforementioned apparatuses. The apparatus 100 of the present disclosure is not limited to the above-described apparatuses.

Various embodiments of the apparatus 100 according to the present disclosure may be combined with each other. The respective embodiments may be combined according to the number of cases. Embodiments of the apparatus 100 obtained by such combination also fall within the scope of the present disclosure. Furthermore, the internal/external components of the apparatus 100 according to the present disclosure described above may be added, changed, replaced, or deleted depending on the embodiments. In addition, the internal/external components of the apparatus 100 described above may be implemented as hardware components.

Figure 4:
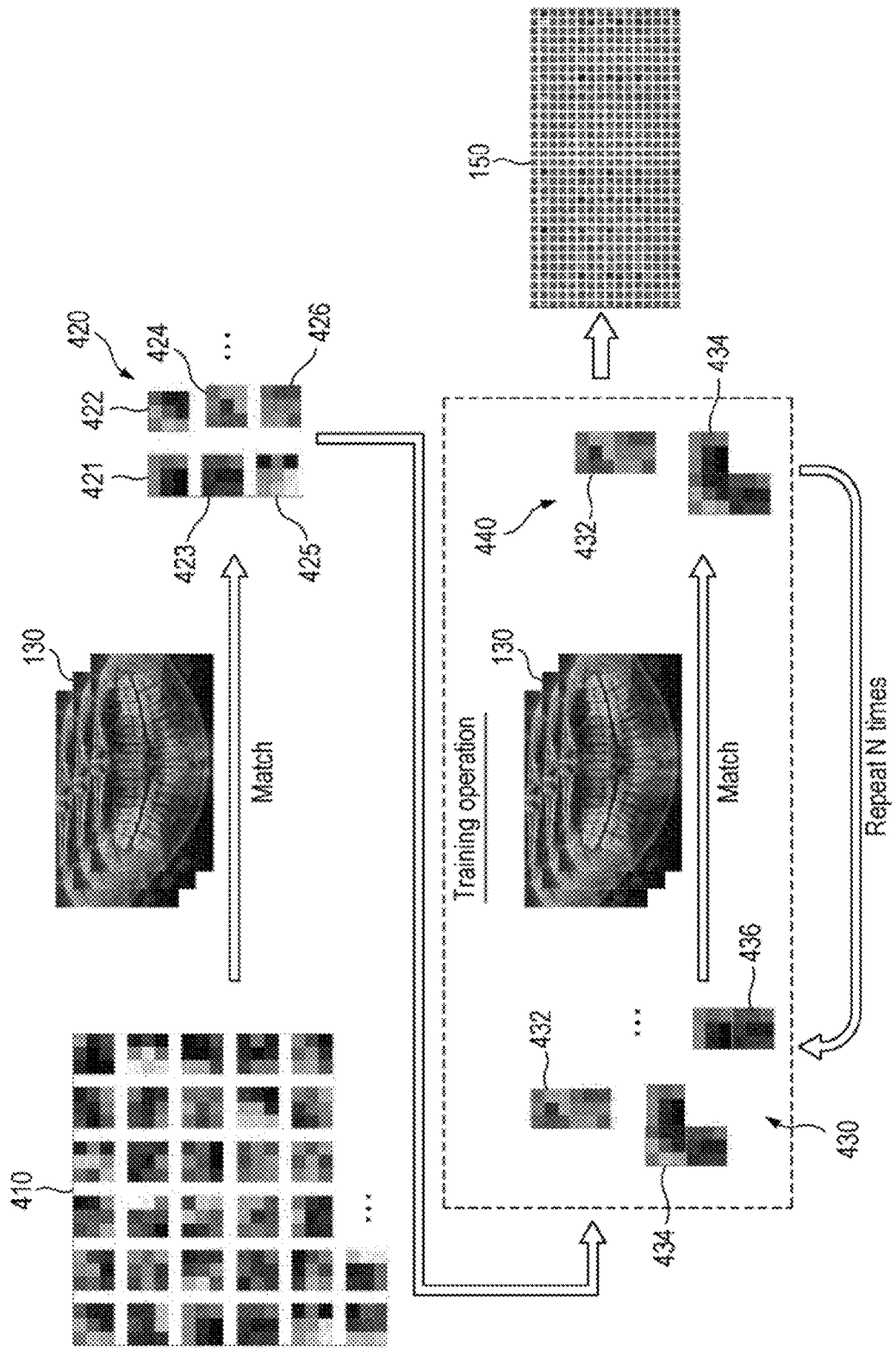
FIG. 4 is a diagram illustrating a process of generating a determination filter according to an embodiment of the present disclosure.

FIG. 4 is a diagram illustrating a process of generating a determination filter 150 according to an embodiment of the present disclosure. In one embodiment, the apparatus 100 may repeat a process of generating a plurality of filters having random pixel values, selecting filters matching a plurality of pre-processed images 130, generating new filters by combining the selected filters, and selecting filters matching the plurality of pre-processed images 130 from among the combined filters. The filter generated after the apparatus 100 repeats the process a predetermined number of times may be determined as the determination filter 150.

Specifically, the processor 310 may generate a plurality of initial filters 410. The initial filter 410 may include two or more pixels. Each pixel of the initial filter 410 may have an arbitrarily (randomly) set pixel value. The illustrated initial filter 410 is illustrated as having 9 pixels. Each pixel is shown to have a contrast according to an arbitrarily set pixel value. In the present disclosure, the pixel value may have a value between 0 and 255. 0 may refer to black, 255 may refer to white, and a value between 0 and 255 may refer to gray having brightness according to the corresponding value.

The processor 310 may select at least two initial filters 420 having matching regions existing in the pre-processed images 130 from among the plurality of initial filters 410. The determination of whether to match may be performed as described above. That is, the pixel values of the region represented by one initial filter and the pixel values of one region of the plurality of pre-processed images 130 are compared with each other. If the pixel values match or exist within a certain range, it may be determined that the matching region of the corresponding initial filter exists in the pre-processed images. For example, in this matching process, the illustrated initial filters 421, 422, 423, 424, 425 and 426 may be selected.

Thereafter, the processor 310 may perform a training operation using at least two of the selected initial filters 410 as first filters. Specifically, the processor 310 may generate a combined filter 430 by combining at least two initial filters used as the first filters. In one embodiment, the processor 310 may generate a combined filter 430 by connecting at least two initial filters horizontally or vertically. For example, the processor 310 may generate a combined filter 432 by connecting the initial filter 424 and the initial filter 426 in the up-down direction. Furthermore, the processor 310 may generate a combined filter 434 by connecting the initial filter 421, the initial filter 422 and the initial filter 423 horizontally or vertically. In addition, the processor 310 may generate a combined filter 436 by connecting the initial filter 421 and the initial filter 423 in the up-down direction.

The processor 310 may compare the combined filters 430 with the plurality of pre-processed images 130, and may select at least two filters 440 having matching regions existing in the plurality of pre-processed images 130 from among the combined filters 430. The determination of whether to match is as described above. For example, among the combined filters 432, 434 and 436, the combined filters 432 and 434 may be selected as filters that match the plurality of pre-processed images 130.

The processor 310 may generate combined filters again by combining the filters 440 selected in the matching process again. For example, the combined filter 432 and the combined filter 434 may be combined to generate a new combined filter. The processor 310 may perform a training operation again using the new combined filters. That is, the processor 310 may reselect at least two filters having matching regions existing in the plurality of pre-processed images 130 from among the new combined filters. The selected filters may be combined again, and may undergo a matching process with the plurality of pre-processed images 130. The processor 310 may repeat the training operation a preset number of times (N times) according to the above-described method.

That is, the training operation may be an operation in which the processor 310 generates combined filters by connecting at least two k-th filters, selects at least two filters each having a matching region in the plurality of pre-processed images 130 from among the combined filters, and determines the selected at least two filters as (k+1)-th filters. The (k+1)-th filters may be used as filters to be combined with each other in a training operation to be performed next.

As described above, after the processor 310 repeats the training operation N times, at least two (N+1)-th filters may be determined. The processor 310 may determine one of the generated two (N+1)-th filters as the determination filter 150. As described above, when the human body having the first gender has teeth corresponding to the first bone age, the determination filter 150 may represent a reference shape of the corresponding teeth.

Figure 5:
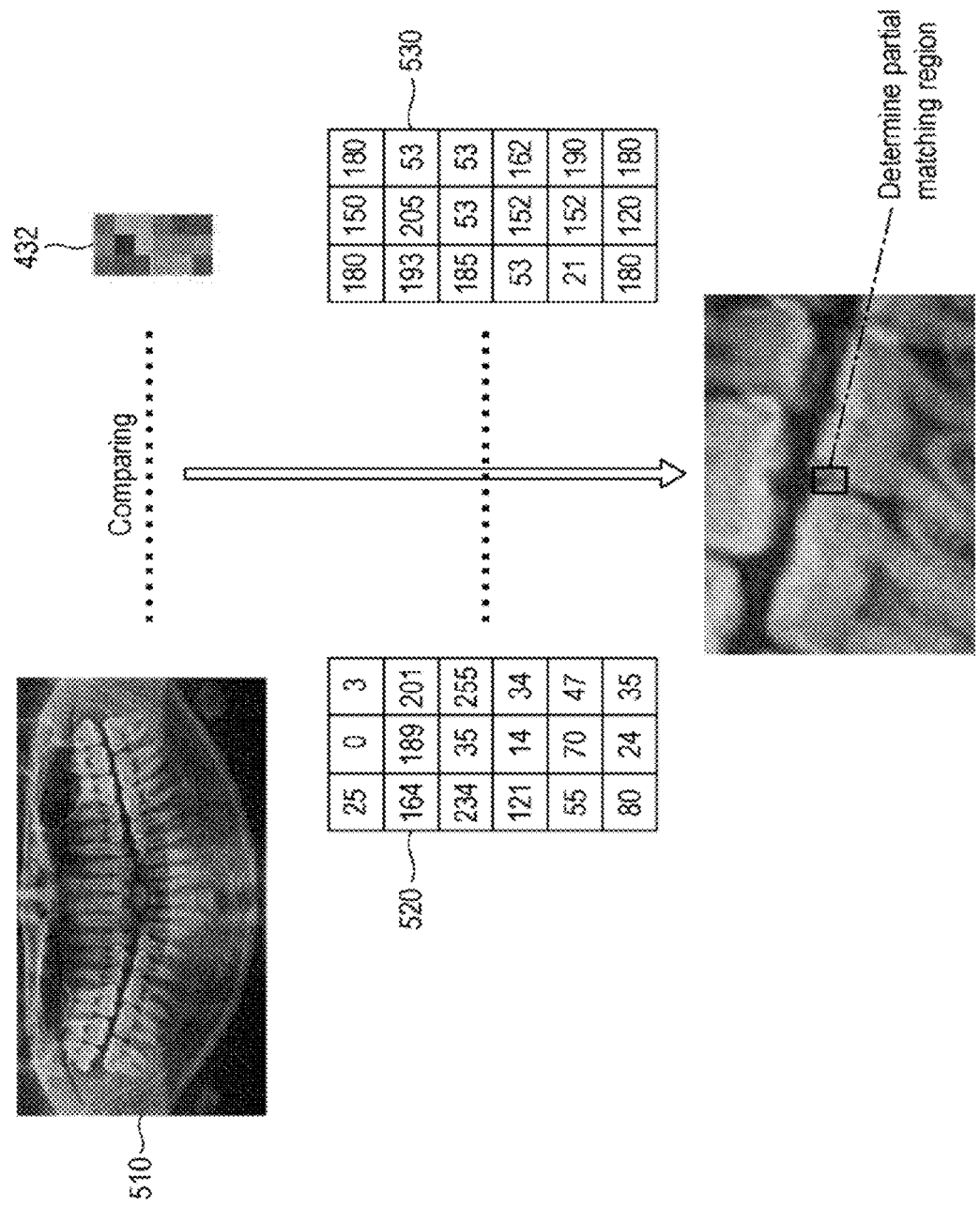
FIG. 5 is a diagram illustrating a process of determining whether a filter has a matching region in an image according to an embodiment of the present disclosure.

FIG. 5 is a diagram illustrating a process of determining whether a filter has a matching region in one image according to an embodiment of the present disclosure. The processor 310 may determine whether one filter (e.g., the initial filter 410, the combined filter 430, the determination filter 150, or the like) has a matching region in one image. In the present disclosure, regardless of the types of the filter and the image, the determination of whether to match may be performed in the same manner. Hereinafter, a process of determining whether to match will be described based on determining whether the combined filter 432 has a matching region in the plurality of pre-processed images 130 in the above-described training operation.

The processor 310 may sequentially or simultaneously compare one filter 432 among the above-described combined filters with the pre-processed images 130. The processor 310 may compare the respective partial regions of the one pre-processed image 510 among the plurality of pre-processed images 130 with the corresponding filter 432. The partial regions of the pre-processed image 510 compared with the filter 432 may have the same number of pixels as the number of pixels of the filter 432.

The processor 310 may perform calculations between the pixel values of each partial region of the pre-processed image 510 and the pixel values of the combined filter 432. For example, the pixel values of the pixels in the partial region of the pre-processed image 510 may be represented as shown in the table 520. In addition, the pixel values of the pixels of the combined filter 432 may be represented as shown in the table 530. In one embodiment, the processor 310 may determine whether the pixel values of the corresponding pixels in two regions match. If the pixel values match, the processor 310 may determine that the two regions match. In one embodiment, the processor 310 may determine whether the pixel values of the corresponding pixels in two regions fall within a preset pixel value range. If the pixel values of the corresponding pixels fall within the preset pixel value range, the processor 310 may determine that the two regions match. For example, when the preset pixel value range is 30, if each of the pixel values of the pixels in one partial region of the pre-processed image 510 and each of the pixel values of the pixels of the combined filter 432 corresponding thereto have a difference value of 30 or less, the processor 310 may determine that the two regions match.

In one embodiment, the processor 310 calculates an average value of deviations of pixel values between one partial region of the pre-processed image 510 and the combined filter 432. If the calculated average value is equal to or less than a preset reference, the processor 310 may determine that the two regions match.

FIG. 6 is a diagram illustrating a process of performing pre-processing by removing a region other than a region representing teeth according to an exemplary embodiment of the present disclosure. As described above, the processor 310 may pre-process each of a plurality of first teeth images 120 to generate each of a plurality of pre-processed images 130. The pre-processing process may be performed in a variety of ways.

In one embodiment, the processor 310 may generate a plurality of pre-processed images 130 by removing a region other than a region 610 representing teeth from each of the plurality of first teeth images 120. The region 610 representing teeth may be a region 610 defined by a preset width 630 and a preset height 640 based on the center point 620 at the bottom of the first teeth image. In general, the shape of teeth may appear at the central lower end in an X-ray image of teeth. By leaving the region having the shape of teeth and removing the remaining region, the region in the image to be compared with the initial filter 410 or the combined filter 430 can be reduced, thereby reducing the calculation burden of the processor 310. Information on the preset width 630 and the preset height 640 may be stored in the memory 320.

In one embodiment, the processor 310 may generate a plurality of pre-processed images 130 by rotating each of the plurality of first teeth images 120. In one embodiment, the processor 310 may generate a plurality of pre-processed images 130 by rotating one first teeth image by at least two preset angles. For example, the processor 310 may obtain a total of seven pre-processed images (including a non-rotated image) by rotating one first teeth image in a clockwise direction by 1, 3 and 5 degrees and rotating the one first teeth image by 1, 3 and 5 degrees in a counterclockwise direction. Information on at least two preset angles may be stored in the memory 320.

Furthermore, in one embodiment, the processor 310 may generate a plurality of pre-processed images 130 by enlarging or reducing each of the plurality of first teeth images 120. In one embodiment, the processor 310 may generate a plurality of pre-processed images 130 by enlarging or reducing one first teeth image within a range of a preset ratio. For example, the processor 310 may enlarge or reduce one first teeth image by 3% or 5% to generate a total of five pre-processed images (including a non-enlarged or non-reduced image). Information on the preset ratio may be stored in the memory 320.

Through the above-described methods, the processor 310 may generate the pre-processed images 130 from the plurality of first teeth images 120 in a larger number than the number of the plurality of first teeth images 120. By increasing the number of the plurality of pre-processed images 130, which is a population to be used for the training of the neural network model 140, the processor 310 can further enhance the accuracy of the determination filter 150 generated in the training process.

FIG. 7 is a diagram illustrating a process of performing pre-processing by removing a portion corresponding to a treatment trace of teeth according to an embodiment of the present disclosure. In the teeth image obtained by imaging teeth, a portion corresponding to the trace of teeth treatment (prosthetic treatment, cavity treatment, artificial crown treatment, etc.) may also appear. The portion corresponding to the treatment trace may be a feature that appears irrespective of the bone age or bone maturity of the corresponding teeth. That is, the trace may not be regarded as a feature that appears only at a specific bone age of teeth, and may be a feature that can appear across all bone ages. When the neural network model 140 is subjected to learning by including such a portion, the accuracy in determining the bone age may be deteriorated. Accordingly, prior to performing the training operation, the portion corresponding to the treatment trace may be removed from the training data.

Specifically, the memory 320 may store information indicating a reference pixel value 710 for identifying a predetermined feature (i.e., a treatment trace) from a plurality of first teeth images 120 or any image representing teeth. In general, a trace of prosthetic treatment or artificial crown treatment may appear as a uniform white color on an X-ray image as compared with general teeth. Accordingly, a reference pixel value 710 for identifying corresponding features represented by a uniform white color or the like may be predefined. In one embodiment, the reference pixel value 710 may be 255, which means white. In one embodiment, the reference pixel value 710 may be defined in the form of a range such as "220 or more", or the like.

The processor 310 may generate a reference filter 720 based on the reference pixel value 710. The reference filter 720 may include one or more pixels, and each pixel may have a reference pixel value 710 (e.g., a). The processor 310 may identify a region matching the reference filter 720 in each of the plurality of first teeth images 120. The determination of whether to match may be performed as described above. The processor 310 may generate each of the plurality of pre-processed images 130 by removing the identified region from each of the plurality of first teeth images 120.

FIG. 8 is a diagram illustrating a process of generating a pre-processed image 130 from a first teeth image 120 according to an embodiment of the present disclosure. Depending on the teeth imaging environment, the first teeth image 120 may have been captured in an inclined state. In addition, depending on the teeth imaging environment, the first teeth image 120 may have been captured to represent target teeth to be larger or smaller. In order to compensate for this difference, in the pre-processing process, the processor 310 may adjust the first teeth image 120 according to a preset reference. Further, in one embodiment, a part of the above-described pre-processing process may be performed by being included in the pre-processing process according to the present example.

Specifically, the memory 320 may store information indicating a reference slope and a reference size for teeth shapes of a plurality of pre-processed images 130. That is, in order to perform an efficient training operation, information indicating the reference slope and the reference size to be possessed by each of the plurality of pre-processed images 130 may be stored in the memory 320. In addition, the memory 320 may further store information indicating a reference pixel value 710 for identifying a predetermined (preset) feature (the treatment trace of the teeth described above).

The processor 310 may rotate each of the plurality of first teeth images 120 so that a teeth shape of each of the plurality of first teeth images 120 has the reference slope stored in the memory 320 (810). Thus, the processor 310 may rotate the teeth shape, which is imaged in an inclined state, so as to conform to the reference slope (e.g., vertical).

The processor 310 may enlarge or reduce each of the plurality of rotated images so that the teeth shape of each of the plurality of rotated images has the reference size stored in the memory 320 (820). In this example, the plurality of rotated images may be enlarged so as to conform to the reference size.

The processor 310 may remove a region other than the region 610 representing the teeth from each of the plurality of enlarged or reduced images (830). As described above, the region 610 representing the teeth may be a region having a preset width and height based on a center point of a lower end of each of the plurality of enlarged or reduced images.

The processor 310 may remove a region matching the reference filter 720 from each of the plurality of images from which the region other than the region 610 representing the teeth has been removed (840). As described above, the reference filter 720 may be generated based on the reference pixel value 710. The processor 310 may remove the regions identified by the reference filter 720 from each of the plurality of images from which the region other than the region 610 representing teeth has been removed.

FIG. 9 is a diagram showing an embodiment of a method for determining a bone age of teeth, which can be performed by the apparatus 100 according to the present disclosure. The method for determining the bone age of teeth according to the present disclosure may be a computer-implemented method. Although the respective steps of the method or algorithm according to the present disclosure have been described in a sequential order in the illustrated flowchart, the respective steps may be performed in an order that can be arbitrarily combined by the present disclosure, in addition to being performed sequentially. The description in accordance with this flowchart does not exclude making changes or modifications to the method or algorithm, and does not imply that any step is necessary or desirable. In one embodiment, at least some of the steps may be performed in parallel, repetitively or heuristically. In one embodiment, at least some of the steps may be omitted, or other steps may be added.

The apparatus 100 according to the present disclosure may perform a method for determining a bone age of teeth according to various embodiments of the present disclosure. The method for determining the bone age of teeth according to an embodiment of the present disclosure may include step S910 of acquiring a plurality of first teeth images, step S920 of generating a plurality of pre-processed images, step S930 of generating a determination filter, step S940 of acquiring a second teeth image and gender information, and/or step S950 of determining a second bone age.

In step S910, the processor 310 of the apparatus 100 may acquire a plurality of first teeth images 120 of a plurality of teeth, each of which corresponds to a first gender and has a first bone age. In step S920, the processor 310 may generate the plurality of pre-processed images 130 by pre-processing the plurality of first teeth images 120. In step S930, the processor 310 may generate a determination filter 150 for determining a teeth shape for the first bone age of a human body having the first gender by training the neural network model 140 for determining the bone age of teeth using the plurality of pre-processed images 130. In step S940, the processor 310 may acquire the second teeth image 210 of teeth of a human body having a second gender and gender information indicating the second gender. In step S950, the processor 310 may determine the second bone age of the teeth corresponding to the second teeth image 210 based on the second teeth image 210 and the gender information by using the determination filter 150.

In one embodiment, step S950 may include determining, by the processor 310, whether the second gender matches the first gender, upon determining that the second gender matches the first gender, determining whether a region matching the determination filter 150 exists in the second teeth image 210, and/or upon determining that the region matching the determination filter 150 exists, determining the first bone age as the second bone age.

In one embodiment, step S930 may include generating, by the processor 310, a plurality of initial filters 410 including two or more pixels each having a randomly set pixel value, selecting at least two initial filters each having a matching region in the plurality of pre-processed images 130 from among the plurality of initial filters 410, repeating a training operation N times by using the at least two initial filters as first filters, and/or determining one of at least two (N+1)-th filters determined by repeating the training operation as a determination filter 150. The training operation may be an operation that generates combined filters by connecting at least two k-th filters and determines at least two of the combined filters each having a matching region in the plurality of pre-processed images 130 as (k+1)-th filters. N may be a preset constant.

In one embodiment, in the training operation, the processor 310 may generate combined filters by connecting at least two k-th filters horizontally or vertically.

In one embodiment, in the training operation, the processor 310 may determine whether each of the combined filters has a matching region in the plurality of pre-processed images 130, based on a calculation result between pixel values of a partial region in each of the plurality of pre-processed images 130 and pixel values of each of the combined filters.

In one embodiment, step S920 may include generating the plurality of pre-processed images 130 by removing, by the processor 310, a region other than the region 610 representing the teeth from each of the plurality of first teeth images 120.

In one embodiment, step S920 may include generating the plurality of pre-processed images 130 in a number larger than the number of the plurality of first teeth images 120 by rotating, by the processor 310, each of the plurality of first teeth images 120 at two or more predetermined angles.

In one embodiment, step S920 may include generating each of the plurality of pre-processed images 130 in a number larger than the number of the plurality of first teeth images 120 by enlarging or reducing, by the processor 310, each of the plurality of first teeth images 120 within a range of a preset ratio.

In one embodiment, step S920 may include generating, by the processor 310, a reference filter 720 including one or more pixels having a reference pixel value 710, identifying a region matching the reference filter 720 in each of the plurality of first teeth images 120, and/or generating the plurality of pre-processed images 130 by removing the identified region from each of the plurality of first teeth images 120.

In one embodiment, step S920 may include rotating, by the processor 310, each of the plurality of first teeth images 120 so that a teeth shape of each of the plurality of first teeth images 120 has a reference slope, enlarging or reducing each of the plurality of rotated images so that a teeth shape of each of the plurality of rotated images has a reference size, removing a region other than the region 610 representing the teeth from each of the plurality of enlarged or reduced images, and/or generating the plurality of pre-processed images 130 by removing a region matching the reference filter 720 including one or more pixels having a reference pixel value 710 from each of the plurality of images from which the region other than the region 610 representing the teeth is removed. The region 610 representing the teeth may be a region having a preset width and height based on a center point of a lower end of each of the plurality of enlarged or reduced images.

Various embodiments of the present disclosure may be implemented as software recorded on a machine-readable recording medium. The software may be software for implementing the various embodiments of the present disclosure described above. The software may be inferred from various embodiments of the present disclosure by programmers in the art to which the present disclosure belongs. For example, the software may be instructions (e.g., code or code segments) or programs that can be read by a device. The device is a device capable of operating according to instructions called from a recording medium, and may be, for example, a computer. In one embodiment, the device may be the electronic apparatus 100 according to embodiments of the present disclosure. In an embodiment, the processor of the device may execute the called instructions so that components of the device can perform a function corresponding to the instructions. In one embodiment, the processor may be the processor 310 according to the embodiments of the present disclosure. The recording medium may refer to any type of device-readable recording medium in which data is stored. The recording medium may include, for example, a ROM, a RAM, a CD-ROM, a magnetic tape, a floppy disk, an optical data storage device, and the like. In one embodiment, the recording medium may be the memory 320. In one embodiment, the recording medium may be implemented in a distributed form in computer systems connected by a network. The software may be distributed, stored and executed in a computer system or the like. The recording medium may be a non-transitory recording medium. The non-transitory recording medium refers to a tangible medium irrespective of whether data is stored semi-permanently or temporarily, and does not include a signal propagating in a transitory manner.

Although the technical content of the present disclosure has been described by the examples described in some embodiments and illustrated in the accompanying drawings, it should be noted that various substitutions, modifications, and changes can be made without departing from the scope of the present disclosure which can be understood by those having ordinary skill in the art to which the present disclosure pertains. In addition, it should be noted that such substitutions, modifications and changes are intended to fall within the scope of the appended claims.

What is claimed is:

1. An apparatus, comprising:
one or more processors; and
one or more memories configured to store instructions for causing the one or more processors to perform an operation when executed by the one or more processors, and a neural network model for determining a bone age of teeth,
wherein the one or more processors are configured to:
acquire a plurality of first teeth images of a plurality of teeth corresponding to a first gender and having a first bone age;
generate a plurality of pre-processed images by pre-processing the plurality of first teeth images;
generate a determination filter for determining a teeth shape for the first bone age of a human body having the first gender by training the neural network model using the plurality of pre-processed images;
acquire a second teeth image of teeth of a human body having a second gender and gender information indicating the second gender; and
determine a second bone age of the teeth corresponding to the second teeth image based on the second teeth image and the gender information by using the determination filter.

2. The apparatus of claim 1, wherein the one or more processors are further configured to:
determine whether the second gender matches the first gender;
upon determining that the second gender matches the first gender, determine whether a region matching the determination filter exists in the second teeth image; and
upon determining that the region matching the determination filter exists, determine the first bone age as the second bone age.

3. The apparatus of claim 2, wherein the one or more processors are further configured to:
generate a plurality of initial filters including two or more pixels each having a randomly set pixel value;
select at least two initial filters each having a matching region in the plurality of pre-processed images from among the plurality of initial filters;
repeatedly perform a training operation N times by using the at least two initial filters as first filters, the training operation being an operation that generates combined filters by connecting at least two k-th filters and determines at least two of the combined filters each having a matching region in the plurality of pre-processed images as (k+1)-th filters; and
determine one of at least two (N+1)-th filters determined by repeating the training operation as the determination filter, the N being a preset constant.

4. The apparatus of claim 3, wherein the one or more processors are further configured to:
in the training operation, generate the combined filters by connecting the at least two k-th filters horizontally or vertically.

5. The apparatus of claim 3, wherein the one or more processors are further configured to:
in the training operation, determine whether each of the combined filters has a matching region in the plurality of pre-processed images based on a calculation result between pixel values of a partial region in each of the plurality of pre-processed images and pixel values of each of the combined filters.

6. The apparatus of claim 1, wherein the one or more processors are further configured to:
generate the plurality of pre-processed images by removing a region other than a region representing teeth from each of the plurality of first teeth images, and
wherein the region representing the teeth is a region having a preset width and height based on a center point of a lower end of each of the plurality of first teeth images.

7. The apparatus of claim 1, wherein the one or more processors are further configured to:
generate the plurality of pre-processed images in a number larger than the number of the plurality of first teeth images by rotating each of the plurality of first teeth images at two or more predetermined angles.

8. The apparatus of claim 1, wherein the one or more processors are further configured to:
generate the plurality of pre-processed images in a number larger than the number of the plurality of first teeth images by enlarging or reducing each of the plurality of first teeth images within a range of a preset ratio.

9. The apparatus of claim 1, wherein the one or more memories are further configured to store information indicating a reference pixel value for identifying a preset feature in the plurality of first teeth images, and
wherein the one or more processors are further configured to:
generate a reference filter including one or more pixels having the reference pixel value;
identify a region matching the reference filter in each of the plurality of first teeth images; and
generate the plurality of pre-processed images by removing the identified region from each of the plurality of first teeth images.

10. The apparatus of claim 1, wherein the one or more memories are further configured to store information indicating a reference slope and a reference size for teeth shapes of the plurality of pre-processed images, and information indicating a reference pixel value for identifying a preset feature, and
  wherein the one or more processors are further configured to:
  rotate each of the plurality of first teeth images so that a teeth shape of each of the plurality of first teeth images has the reference slope;
  enlarge or reduce each of the plurality of rotated images so that a teeth shape of each of the plurality of rotated images has the reference size;
  remove a region other than a region representing teeth from each of the plurality of enlarged or reduced images, the region representing the teeth being a region having a preset width and height based on a center point of a lower end of each of the plurality of enlarged or reduced images; and
  generate the plurality of pre-processed images by removing a region matching the reference filter including one or more pixels having the reference pixel value from each of the plurality of images from which the region other than the region representing the teeth is removed.

11. A method performed in a computer including one or more processors and one or more memories that are configured to store instructions to be executed by the one or more processors, the method comprising:
  acquiring a plurality of first teeth images of a plurality of teeth corresponding to a first gender and having a first bone age;
  generating a plurality of pre-processed images by pre-processing the plurality of first teeth images;
  generating a determination filter for determining a teeth shape for the first bone age of a human body having the first gender by training a neural network model for determining a bone age of teeth using the plurality of pre-processed images;
  acquiring a second teeth image of teeth of a human body having a second gender and gender information indicating the second gender; and
  determining a second bone age of the teeth corresponding to the second teeth image based on the second teeth image and the gender information by using the determination filter.

12. The method of claim 11, wherein determining the second bone age includes:
  determining whether the second gender matches the first gender;
  upon determining that the second gender matches the first gender, determining whether a region matching the determination filter exists in the second teeth image; and
  upon determining that the region matching the determination filter exists, determining the first bone age as the second bone age.

13. The method of claim 12, wherein generating the determination filter includes:
  generating a plurality of initial filters including two or more pixels each having a randomly set pixel value;
  selecting at least two initial filters each having a matching region in the plurality of pre-processed images from among the plurality of initial filters;
  repeatedly performing a training operation N times by using the at least two initial filters as first filters, the training operation being an operation that generates combined filters by connecting at least two k-th filters and determines at least two of the combined filters each having a matching region in the plurality of pre-processed images as (k+1)-th filters; and
  determining one of at least two (N+1)-th filters determined by repeating the training operation as the determination filter, the N being a preset constant.

14. The method of claim 11, wherein generating the plurality of pre-processed images includes:
  generating the plurality of pre-processed images by removing a region other than a region representing teeth from each of the plurality of first teeth images, and
  wherein the region representing the teeth is a region having a preset width and height based on a center point of a lower end of each of the plurality of first teeth images.

15. The method of claim 11, wherein generating the plurality of pre-processed images includes:
  generating a reference filter including one or more pixels having a reference pixel value;
  identifying a region matching the reference filter in each of the plurality of first teeth images; and
  generating the plurality of pre-processed images by removing the identified region from each of the plurality of first teeth images, and
  wherein the reference pixel value is a pixel value for identifying a preset feature in the plurality of first teeth images.

16. A non-transitory computer-readable recording medium that stores instructions for causing one or more processors to perform an operation when executed by the one or more processors, wherein the instructions cause the one or more processors to perform:
  acquiring a plurality of first teeth images of a plurality of teeth corresponding to a first gender and having a first bone age;
  generating a plurality of pre-processed images by pre-processing the plurality of first teeth images;
  generating a determination filter for determining a teeth shape for the first bone age of a human body having the first gender by training a neural network model for determining a bone age of teeth using the plurality of pre-processed images;
  acquiring a second teeth image of teeth of a human body having a second gender and gender information indicating the second gender; and
  determining a second bone age of the teeth corresponding to the second teeth image based on the second teeth image and the gender information by using the determination filter.

17. The recording medium of claim 16, wherein the instructions cause the one or more processors to perform:
  determining whether the second gender matches the first gender;
  upon determining that the second gender matches the first gender, determining whether a region matching the determination filter exists in the second teeth image; and
  upon determining that the region matching the determination filter exists, determining the first bone age as the second bone age.

18. The recording medium of claim 17, wherein the instructions cause the one or more processors to perform:
  generating a plurality of initial filters including two or more pixels each having a randomly set pixel value;

selecting at least two initial filters each having a matching region in the plurality of pre-processed images from among the plurality of initial filters;

repeatedly performing a training operation N times by using the at least two initial filters as first filters, the training operation being an operation that generates combined filters by connecting at least two k-th filters and determines at least two of the combined filters each having a matching region in the plurality of pre-processed images as (k+1)-th filters; and determining one of at least two (N+1)-th filters determined by repeating the training operation as the determination filter, the N being a preset constant.

19. The recording medium of claim 16, wherein the instructions cause the one or more processors to perform:

generating the plurality of pre-processed images by removing a region other than a region representing teeth from each of the plurality of first teeth images, and wherein the region representing the teeth is a region having a preset width and height based on a center point of a lower end of each of the plurality of first teeth images.

20. The recording medium of claim 16, wherein the instructions cause the one or more processors to perform:

generating a reference filter including one or more pixels having a reference pixel value;

identifying a region matching the reference filter in each of the plurality of first teeth images; and generating the plurality of pre-processed images by removing the identified region from each of the plurality of first teeth images, and wherein the reference pixel value is a pixel value for identifying a preset feature in the plurality of first teeth images.

* * * * *